United States Patent

Schaefer et al.

Patent Number: 5,189,184
Date of Patent: Feb. 23, 1993

[54] 2-(3'-BUTENYL)-3,4-DIHYDRO-2H-PYRANS, THEIR SYNTHESIS AND USE

[75] Inventors: Dietmar Schaefer, Hattingen; Andreas Weier; Christian Weitemeyer, both of Essen; Dietmar Wewers, Bottrop, all of Fed. Rep. of Germany

[73] Assignee: Th. Goldschmidt AG, Essen, Fed. Rep. of Germany

[21] Appl. No.: 736,766

[22] Filed: Jul. 29, 1991

[30] Foreign Application Priority Data

Aug. 30, 1990 [DE] Fed. Rep. of Germany ....... 4027436

[51] Int. Cl.$^5$ ............................................. C07D 315/00
[52] U.S. Cl. ........................................................ 549/427
[58] Field of Search ........................................... 549/427

[56] References Cited

U.S. PATENT DOCUMENTS

| | | | |
|---|---|---|---|
| 4,122,291 | 10/1978 | Kyo et al. | 568/887 |
| 4,173,551 | 11/1979 | Crivello | 428/542 |
| 4,518,788 | 5/1985 | Crivello | 560/64 |
| 4,617,238 | 10/1986 | Crivello et al | 528/423 |
| 4,705,887 | 11/1987 | Crivello | 560/190 |

FOREIGN PATENT DOCUMENTS

| | | | |
|---|---|---|---|
| 59-25385 | 7/1984 | Japan | 549/427 |
| 910913 | 11/1962 | United Kingdom | 549/427 |

OTHER PUBLICATIONS

"Geschwindigkeitsbestimmende Faktoren bei der kationischen UV-Härtung", pp. 803–807, by J. V. Crivello.

*Primary Examiner*—Alan L. Rotman
*Assistant Examiner*—Raymond Covington
*Attorney, Agent, or Firm*—Anderson Kill Olick & Oshinsky

[57] ABSTRACT

2-(3'-butenyl)-3,4-dihydro-2H-pyrans of the general formula

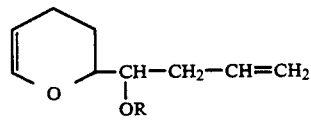

wherein R is a hydrogen group or an alkyl group with 1 to 6 carbon atoms. Methods for the synthesis of these compounds and their use as reactive modifiers or diluents for cationically curable monomers or polymers.

5 Claims, No Drawings

2-(3'-BUTENYL)-3,4-DIHYDRO-2H-PYRANS, THEIR SYNTHESIS AND USE

FIELD OF INVENTION

The present invention is directed to novel, cationically curable 2-(3'-butenyl)-3,4-dihydro-2H-pyrans and their synthesis. Considered from another aspect, the invention is concerned with cationically curable casting compositions or coating materials for planar supports as well as reactive modifiers or diluents for cationically curable monomers or polymers on the basis of novel pyrans.

BACKGROUND INFORMATION AND PRIOR ART

Aside from those systems, which cure under the action of UV by a free radical polymerization, systems containing cationically curable vinyl compounds have been developed in recent years, for which the curing is initiated, in particular, by diaryliodonium and triarylsulfonium salts. The advantage of the cationically curing systems lies in the insensitivity of the curing reaction to the effects of oxygen of the air, the rapid formation of a film and the nonpolluting nature of these systems.

The cationic curing of vinyl monomers is described in U.S. Pat. Nos. 4,617,238, 4,518,788 and 4,705,887.

For such a curing reaction, UV-curable vinyl ether compounds have gained special attention because they are cured rapidly and processed economically and they do not contaminate the environment. Such vinyl ether compounds can be synthesized in various ways. In a survey article of the "Rate-Determining Factors in Cationic UV Curing" in the Journal, Farbe und Lack, 1987, pages 803 to 807, the following possible syntheses are given:

1. Base-catalyzed addition reaction of Reppe between acetylene and diols

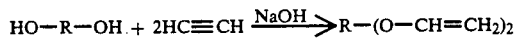

2. Phase transfer-catalyzed condensation of 2-chloroethyl vinyl ether and diols

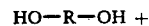

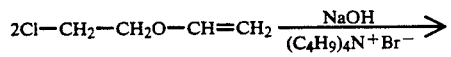

3. Catalyzed rearrangement of the bis(allyl ether) to the corresponding bis(methyl vinyl ether)

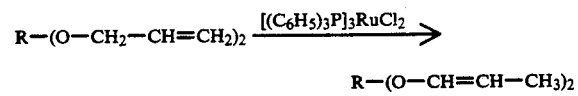

The Reppe addition reaction cannot be realized economically. For the second reaction, 2-chloroethyl ether is required, the use of which is undesirable for physiological reasons.

It is a disadvantage, common to vinyl ethers, that, in the presence of moisture and traces of acid, these enol ethers split into low-boiling, highly odoriferous carbonyl compounds:

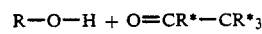

R* = H— or the alkyl group.

OBJECTS OF THE INVENTION

It is an object of the invention to solve the technical problem of making available additional cationically curable compounds, which can be used themselves or as reactive modifiers or diluents for cationically curable monomers or polymers and do not release any low boiling, highly odoriferous carbonyl compounds under comparable conditions. At the same time, it shall be possible to synthesize the cationically curable compounds in a simple and economic manner.

SUMMARY OF THE INVENTION

The inventive, novel, cationically curable compounds correspond to the general formula

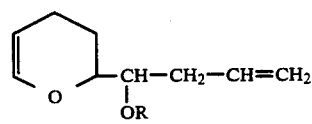

wherein R is hydrogen or an alkyl group with 1 to 6 carbon atoms.

Examples of suitable R alkyl groups are the methyl, ethyl, propyl, isopropyl, butyl, isobutyl, pentyl and hexyl groups. Particularly preferred are the linear alkyl groups, especially the ethyl and propyl groups.

The compounds below are particularly preferred:

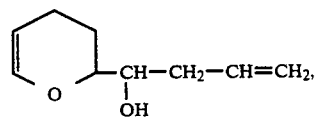

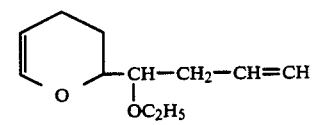

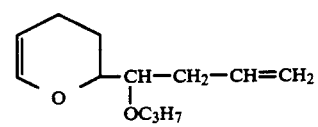

A further aspect of the invention is the synthesis of the inventive, novel compounds. The inventive method is characterized in that, either a) 2-formyldihydropyran is reacted with allyl magnesium halide in a molar ratio of 1:0.8 to 1:1.3 in the presence of an ether or ether/alkane mixture as solvent at a temperature within the range from between about −80° to +80° C. or b) 2-formyldihydropyran is reacted with allyl lithium in a molar ratio of 1:1 to 1:1.3 in the presence of an ether or an ether/alkane mixture as solvent at a temperature within the range from between about −80° to +70° C., and c) the reaction product obtained in a) or b) is hydrolyzed and subsequently, in the event that $R^2$ is an alkyl group, etherified in a known manner with a halide of formula $R^2X$ (X=halogen).

Method step a) proceeds in a known manner as A Grignard reaction, for which the known solvents for such a reaction can be used. These solvents are, primarily, ethers, such as tetrahydrofuran or diethyl ether or the mixture of these ethers with alkanes, such as hexane. The preferred temperature range is 30° to 70° C. For the hydrolysis, it is advisable to pour the reaction mixture into ice water. The reaction mixture is separated as an oily phase from the water and can then be purified in the usual way, for example, by distillation.

Method step b) also proceeds in the presence of ethers or ether/alkane mixtures as solvent. The preferred temperature range is −80° to +20° C. The etherification in step c) also take place in a known manner by the reaction of the reaction products with alkyl halides at about 20° to 100° C.

The inventive compounds are crystal clear liquids of low viscosity.

A further aspect of the invention is the use of the inventive substances as cationically curable casting compositions or coating materials for flat or planar supports or as reactive modifiers for cationically curable monomers or polymers.

The inventive compounds are cured preferably by UV radiation in the presence of catalysts, such as salt-like diaryliodonium or triarylsulfonium compounds or non-salt-like compounds, such as ketosulfones. Examples of such hardeners are

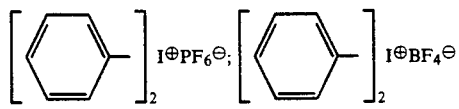

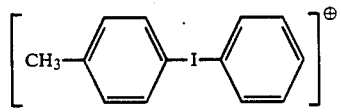

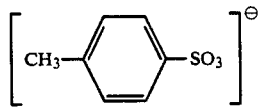

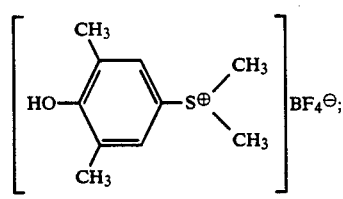

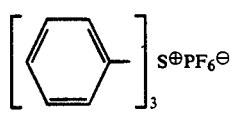

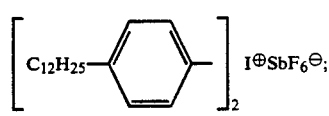

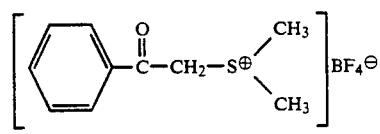

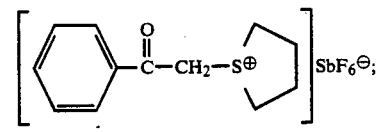

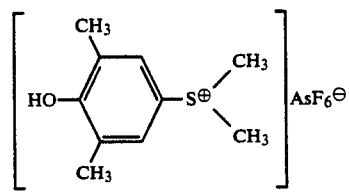

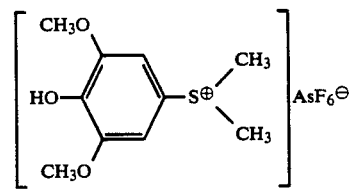

Particularly preferred initiators are:

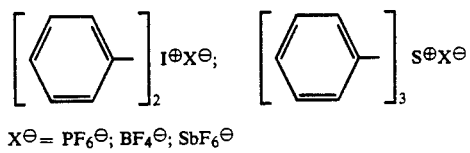

$X^\ominus = PF_6^\ominus; BF_4^\ominus; SbF_6^\ominus$

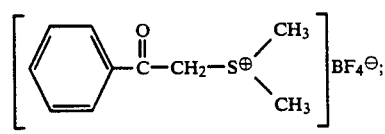

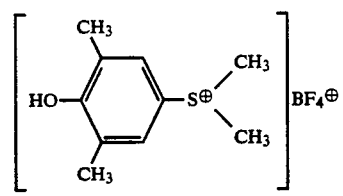

Moreover, heat curing using onium salts and organic oxidizing agents or soluble copper salts or chelates is possible. This is described, for example in U.S. Pat. No. 4,173,551. Another possibility for bringing about curing is the use of compounds, which release acids or Lewis acids at elevated temperatures. Such compounds are, in particular, sulfonic acid salts, especially amine salts, sulfonate esters and amine complexes of Lewis acids, such as the boric acid trifluoride triethylamine complex.

The curing agents are added to the inventive compounds in amounts of about 0.1 to 5% by weight.

The inventive compounds can be mixed with conventional additives, such as fillers, pigments, flame retardants and the like.

The curable compounds or their preparations can be applied on substrates such as metal, rubber, plastic, paper, wood, glass fabric, cement, ceramic, etc.

The inventive compounds can be mixed with polymers, which either themselves are cationically curable or have reactive groups, which can react with the terminal double bond of the inventive compounds. Examples of such polymers are propenyl polyethers, vinyl polyether polysiloxanes, hydrocarbons or organosilicon compounds containing epoxy groups, styrene and hydrogensiloxanes (in the presence of transition metal catalysts).

The synthesis of the inventive compounds and their application properties are shown and explained in greater in the following examples, it being understood that these examples are given by way of explanation and not by way of limitation.

EXAMPLE 1

To 48 g (2.0 moles) of magnesium shavings in 400 mL of a 5:3 mixture of anhydrous THF and diethyl ether, a mixture of 242 g (2.0 moles) of allyl bromide and 179.2 g of 2-formyldihydropyran is slowly added dropwise, so that the reaction mixture boils continuously. After the addition, refluxing is continued for a further 5 hours. After that, the reaction mixture is added to 1 L of ice water, the organic phase is separated and the aqueous phase is diluted with 200 mL of saturated ammonium chloride solution and washed with 200 mL of hexane. The combined organic phases are dried over magnesium sulfate, filtered and distilled. A colorless liquid is obtained in an amount of 129 g, which corresponds to 52% of the theoretical yield. This liquid has a boiling point of 85° C. at 2.7 mbar. According to the NMR spectrum, it is 2-(1'-hydroxy-3'-butenyl)-3,4-dihydro-2H-pyran.

EXAMPLE 2

A suspension of 22.56 g (0.4 moles) of powdered KOH in 100 mL of dimethylsulfoxide (DMSO) is stirred for 5 minutes, after which 15.42 g (0.1 moles) of 2-(1'-hydroxy-3'-butenyl)-3,4-dihydro-2H-pyran and 21.8 g (0.2 moles) of ethyl bromide are added rapidly one after the other. After 30 minutes of stirring, the reaction mixture is poured into 500 mL of water and extracted three times with 50 Ml amounts of diethyl ether. The combined organic phases are washed five times with 30 mL amounts of water, dried over magnesium sulfate and distilled. The expected ethyl ether is obtained in a yield of 15.6 g (corresponding to 86% of the theoretical amount).

EXAMPLE 3

As in Example 2, 22.56 g (0.4 moles) of powdered KOH, 15.42 g (0.1 moles) of 2-(1'-hydroxy-3'-butenyl)-3,4-dihydro-2H-pyran and 24.6 g (0.2 moles) of propyl bromide are reacted to form 16.3 g (83% of the theoretical yield) of 2-(1'-propoxy-3'-butenyl)-3,4-dihydro-2H-pyran.

To check the usefulness of the inventive dihydropyrans as reactive diluents, the substances are added to other cationically curable substances (a mixture of bisphenol A diglycidyl ether and triethylene glycol divinyl ether in the ratio of 1:1, which is referred to in the following as "BTE") and, after addition of 2% by weight of a suitable photoinitiator, cured by UV radiation (medium pressure mercury vapor lamp, 80 W/cm) in an aluminum lid, which has a diameter of 50 mm. The thickness of the layer in each case is about 3 mm.

| Substance | Viscosity | Curing | Surface |
|---|---|---|---|
| BTE | 10 cp | 10 s | solid, nongreasy, fragile |
| BTE + 5% Example 1 | 8.0 cp | 9–10 s | solid, nongreasy, inelastic |
| BTE + 10% Example 1 | 7.6 cp | 9–10 s | solid, nongreasy, inelastic |
| BTE + 5% Example 2 | 8.6 cp | 10 s | solid, nongreasy, elastic |
| BTE + 5% Example 3 | 9.0 cp | 10 s | solid, nongreasy, elastic |

The substances cure after being irradiated with UV. The curing is not inhibited by the oxygen from the air.

Because of their relatively acidic protons, alcohols in particular are capable of accelerating the curing rate. The addition of the dihydropyrans changes the surface nature, so that the cured substances are less brittle.

We claim:

1. 2-(3'-butenyl)-3,4-dihydro-2H-pyrans of the general formula

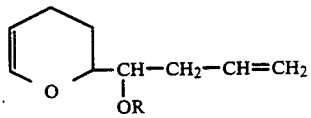

wherein R is hydrogen or an alkyl group with 1 to 6 carbon atoms.

2. A method for the synthesis of 2-(3'-butenyl-3,4-dihydro-2H-pyrans of the general formula

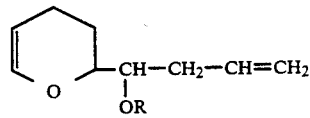

wherein R is hydrogen or an alkyl group with 1 to 6 carbon atoms, which comprises
 a) reacting 2-formyldihydropyran with allyl magnesium halide in a molar ratio of between about 1:0.8 to 1:1.3 in the presence of an ether or ether/alkane mixture as solvent at a temperature within the range from between about −80° to +80° C., and
 b) hydrolyzing the reaction product thus obtained and, subsequently, if R is alkyl, etherifying with a halide of formula RX(X=halogen).

3. The method of claim 2, wherein step a) is carried out at 30° to 70° C.

4. A method for the synthesis of 2-(3'-butenyl)-3,4-dihydro-2H-pyrans of the general formula

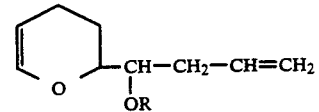

wherein R is hydrogen or alkyl with 1 to 6 carbon atoms which comprises
 a) reacting 2-formyldihydropyran with allyl lithium in a molar ratio of between about 1:0.8 to 1:1.3 in the presence of an ether or an ether/alkane mixture as solvent at a temperature within the range from between about −70° to +70° C., and
 b) hydrolyzing the reaction product thus obtained and, subsequently, if R is alkyl, etherifying with a halide of formula RX(X=halogen).

5. The method of claim 4, wherein step a) is carried out at −80° to +20° C.

* * * * *